(12) United States Patent
Hauge (10) Patent No.: US 6,639,153 B2
(45) Date of Patent: Oct. 28, 2003

(54) PATIENT LEAD WIRE DETANGLER

(75) Inventor: Patrick L. Hauge, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/794,088

(22) Filed: Feb. 28, 2001

(65) Prior Publication Data

US 2002/0117326 A1 Aug. 29, 2002

(51) Int. Cl.[7] ................................................. H01B 1/00
(52) U.S. Cl. ....................... 174/135; 174/136; 361/826
(58) Field of Search ................................ 174/135, 136, 174/154, 70 A, 72 R, 72, 72 A, 95, 97, 138 E; 361/826; 128/908, 912; 606/41

(56) References Cited

U.S. PATENT DOCUMENTS

| | | | | |
|---|---|---|---|---|
| 4,159,395 A | * | 6/1979 | Cogelia ........................ 150/154 |
| 4,697,593 A | * | 10/1987 | Evans et al. ................... 356/41 |
| 4,771,743 A | * | 9/1988 | McDowell ............... 123/143 C |
| 4,896,667 A | * | 1/1990 | Magnuson et al. ..... 128/207.14 |
| 4,993,065 A | * | 2/1991 | Chiou ........................ 379/430 |
| 5,233,986 A | * | 8/1993 | Robson ........................ 607/27 |
| 5,562,710 A | * | 10/1996 | Olsen et al. ................. 439/909 |
| 5,569,882 A | * | 10/1996 | Yokoyama et al. ....... 174/138 F |
| 5,600,873 A | * | 2/1997 | May ........................... 200/330 |
| 5,623,131 A | * | 4/1997 | Earnest ................ 128/DIG. 15 |
| 5,685,303 A | | 11/1997 | Rollman et al. |
| 5,711,055 A | * | 1/1998 | Quick ....................... 24/129 R |
| 5,813,979 A | | 9/1998 | Wolfer |
| 5,943,293 A | * | 8/1999 | Luscombe et al. ........ 174/101.5 |
| 6,090,075 A | * | 7/2000 | House .......................... 604/172 |
| 6,184,474 B1 | * | 2/2001 | Craft, Jr. ..................... 174/135 |

* cited by examiner

Primary Examiner—Dean A. Reichard
Assistant Examiner—Jinhee Lee (57) ABSTRACT

A device for detangling or preventing the tangling of a plurality of elongated flexible members. At least one slidable collar includes at least one elongated bore for receiving the flexible members. The slidable collar is slidable along the flexible members. In an embodiment, the device includes a fixed collar that is fixed to the flexible members; and a retractable sheath surrounds the flexible members and id fixed to the fixed collar and to the slidable collar, wherein sliding the slidable collar along the flexible member away from the fixed collar extends the sheath along the flexible members.

27 Claims, 9 Drawing Sheets

PATIENT LEAD WIRE DETANGLER

FIELD OF THE INVENTION

The present invention relates to a device and method for detangling and preventing the tangling of a plurality of elongated flexible members. In particular, the present invention relates to a device and method for detangling and preventing the tangling of a plurality of leads for operatively connecting electrodes to an electrotherapy and/or monitoring device.

BACKGROUND OF THE INVENTION

The number of electrically operated medical devices has exploded in recent times. Along these lines, more and more monitoring and treatment devices are developed constantly. Most electrically operated medical devices include leads, or wire, that interconnect elements of the devices. For example, a base unit is often interconnected with a portion of the device that interacts with a patient. Along these lines, monitoring and/or treatment electrodes that are attached to a patient can be interconnected with a base unit with one or more leads. Tangled or intertwining of the leads may prevent or hinder a caregiver in administering to a patient. Of course, there are many devices other than medical devices which include leads, and tangling of the leads can hinder or prevent operation of any such device.

One example of devices that utilizes leads to interconnect its elements includes electrotherapy devices used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation ("VF") or shockable ventricular tachycardia ("VT") to a normal sinus rhythm. Similarly, external cardioverters can be used to provide paced shocks to convert atrial fibrillation ("AF") to a more normal heart rhythm.

Sudden cardiac arrest ("SCA") is the leading cause of unanticipated death in the United States. On average about 600 people per day die of SCA. This translates to nearly one death every two minutes. It is likely that these statistics would, at a minimum, hold true for third world countries. Precise international statistics are not available but the U.S. rate for coronary heart disease deaths, of which sudden deaths constitute nearly half, is representative of international rates (rank $16^{th}$ and $13^{th}$ among 36 nations reported by the World Health Organization (WHO), for men and women, respectively).

Most sudden cardiac death is caused by VF, in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. As improved access to defibrillators increases, survival rates from SCA also increase.

The electrical pulse must be delivered within a short time after onset of VF in order for the patient to have any reasonable chance of survival. To be effective, the defibrillation shock must be delivered to the patient within minutes of the onset of VF. Studies have shown that defibrillation shocks delivered within one minute after the onset of VF achieve up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result. Electrical fibrillation may also be used to treat shockable ventricular tachycardia ("VT"). Accordingly, defibrillation is the appropriate therapy for any shockable rhythm, that is, VF or shockable VT.

External defibrillators send electrical pulses to a patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators, collectively referred to as "AEDs", are becoming increasingly popular because relatively inexperienced personnel can use them. U.S. Pat. No. 5,607,454 to Cameron et al., entitled Electrotherapy Method and Apparatus, and PCT publication number WO 94/27674, entitled Defibrillator With Self-Test Features, the specifications of which are hereby incorporated by reference, describe AEDs.

AEDs provide a number of advantages, including the availability of external defibrillation at locations where external defibrillation is not regularly expected, and is likely to be performed quite infrequently, such as in residences, public buildings, businesses, personal vehicles, public transportation vehicles, among other locations.

Monitoring devices are utilized in conjunction with electrotherapy devices to monitor a patient's heart rate. If a patient does not have a shockable rhythm, then a defibrillating shock should not be administered. Just as it is important to quickly administer a defibrillating shock if a patient has a shockable rhythm, it is important to quickly verify that the patient has a shockable rhythm.

SUMMARY OF THE INVENTION

A problem with deploying a device such as a defibrillator/monitor in any location is the tangling of leads extending, for example, between the defibrillator/monitor and electrodes. Tangling of the leads can occur when the device is prepared for storage, as the device is being taken from storage for use, and when preparing the device for restorage. Tangling of the leads can hinder or prevent proper use of the device.

The present invention addresses the above-described problem by providing a device for detangling or preventing the tangling of a plurality of elongated flexible members. The device includes at least one slidable collar that includes at least one bore for receiving the flexible members. The slidable collar is slidable along the flexible members.

Additionally, the present invention provides a device for preventing a plurality of flexible members from becoming tangled. The device includes a flexible member retainer for retaining the flexible members. The flexible member retainer includes a plurality of flexible member retaining grooves. Each groove retains one flexible member. Each groove includes an opening having a maximum width smaller than a maximum width of the flexible member the groove is to retain.

In addition, the present invention provides a method for detangling a plurality of flexible members. According to the method, at least one slidable collar member that includes a bore for each flexible member is moved along the flexible members.

Furthermore, the present invention provides a method for preventing a plurality of flexible members from becoming tangled. According to the method, the flexible members are retained with a flexible member retainer. The flexible member retainer includes a plurality of flexible member retaining grooves. Each groove retains one flexible member and includes an opening having a maximum width smaller than a maximum width of the flexible member the groove is to retain.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DETAILED DESCRIPTION OF THE INVENTION

To facilitate proper operation of an electrotherapy device in general and a defibrillator in particular, the present invention provides a device and a method for detangling and/or preventing the tangling of elongate flexible members, such as lead wires, associated with electrotherapy devices, defibrillators, monitors and/or any other device. Although the present invention is described in relation to lead wires, it could be utilized with any elongate members in any context, not only as lead wires.

To provide a detangling and/or detangling prevention function, a device according to the present invention includes one or more collar members and/or one or more elongate flexible member retainer member. A collar member according to the present invention includes a plurality of flexible member receiving passages, or "bores". The bores may have any cross-sectional shape. Typically, the bores have a similar cross-sectional shape as the flexible members they are to receive. However, the bores could have any shape, such as circular, square, rectangular, triangular, or any other shape.

Similarly, the bore may have any cross-sectional area. However, the bores typically have a cross-sectional area only slightly larger than the cross-sectional area of the elongate flexible members they are to receive. If the bores have a cross-sectional shape similar to the flexible members and a cross-sectional area only slightly larger than the cross-sectional area of the elongate flexible members then the bores typically will permit the collar to slide along the flexible members. The relationship between the bore cross-sectional area and the flexible member cross-sectional area can determine how freely the collar moves along the flexible member(s). The larger the cross-sectional area of the bore, the more freely the collar slides along the flexible member(s). If the cross-sectional area of the bore is just slightly larger than the cross-sectional area of the flexible member(s), then the collar typically will not slide as freely and will have a tendency to remain stationary where it is arranged. In some embodiments, the bores could have a cross-sectional area more than just slightly larger than the cross-sectional area of the flexible members. In such embodiments, flexible member retaining elements could extend from the surface of the bore(s) to engage the flexible members.

One factor that may be considered in the shape and size of the bores is the desired size of the collar member. If it is desired that the collar member have a small size, then the bores typically will have a cross-sectional shape similar to the flexible members and a cross-sectional area only slightly larger than the cross-sectional area of the flexible members.

The length of the collar and the bores may also vary. Typically, the bores have a length of about 0.5 inch to about 1.5 inch. However, the passages may have any length. Shorter passages may permit the collar to slide more easily. However, longer passages may permit the collar to be larger and, therefore, be gripped more easily by a user.

The bores could have any desired arrangement relative to each other in the collar. Along these lines, the bores could be arranged in a line, a triangle, or any other shape. For example, FIGS. 3–5 and 11–13 illustrate embodiments of the present invention that include bores arranged in a line. On the other hand, FIGS. 6–10 illustrate an embodiment of a collar that includes bores arranged in a triangular configuration.

A collar member according to the present invention may be made of any material. One example of a material that may be utilized is a fluoropolymer. For example, polytetrafluoroethylene cPTFE) may be utilized. One example of a PTFE is TEFLON, available from E. I. DuPont de Nemours and Company. Other materials include polycarbonate, polypropylene, nylon, or any other non-ferrous material.

A collar member may be formed as a single unitary member. Alternatively, a collar member according to the present invention may be formed of a plurality of members. For example, each bore may be formed as a tube. According to such an embodiment, the body of the collar member may be formed from one or more elements. Along these lines, the collar may be formed from a single "shell" member that the tubes are inserted into. Alternatively, the collar member "shell" may include a plurality of submembers that are joined together and to the receiving passage tubes.

Figure 1:
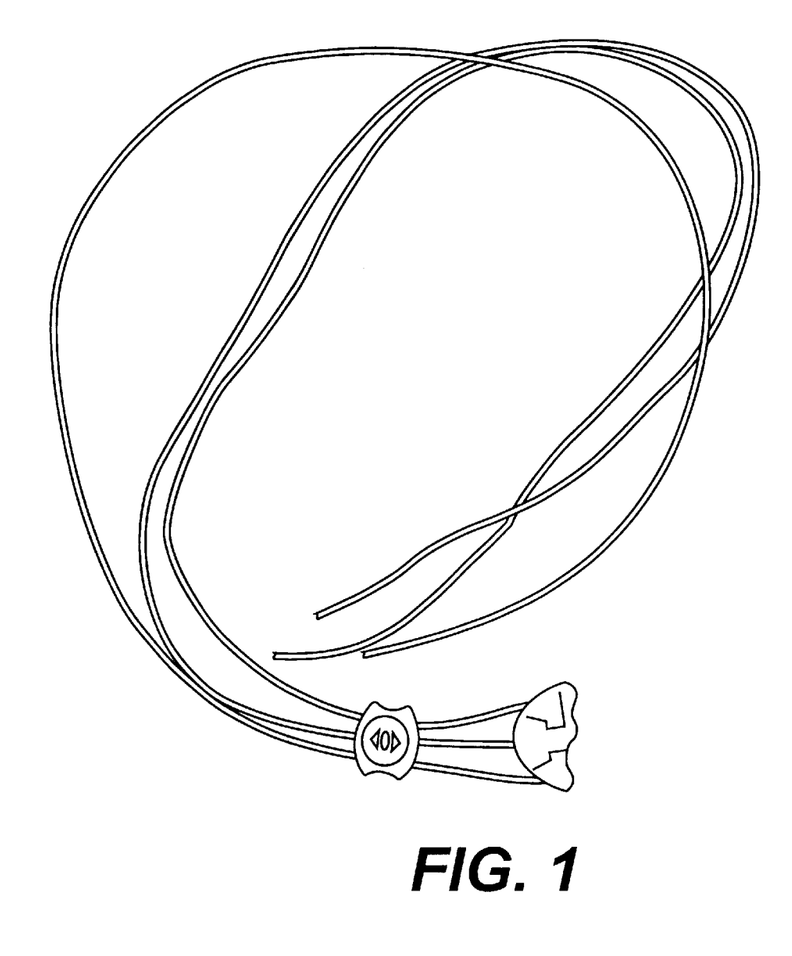
FIG. 1 represents a perspective view of an embodiment of a device for detangling a plurality of elongate flexible members according to the present invention.
Figures 2, 3:
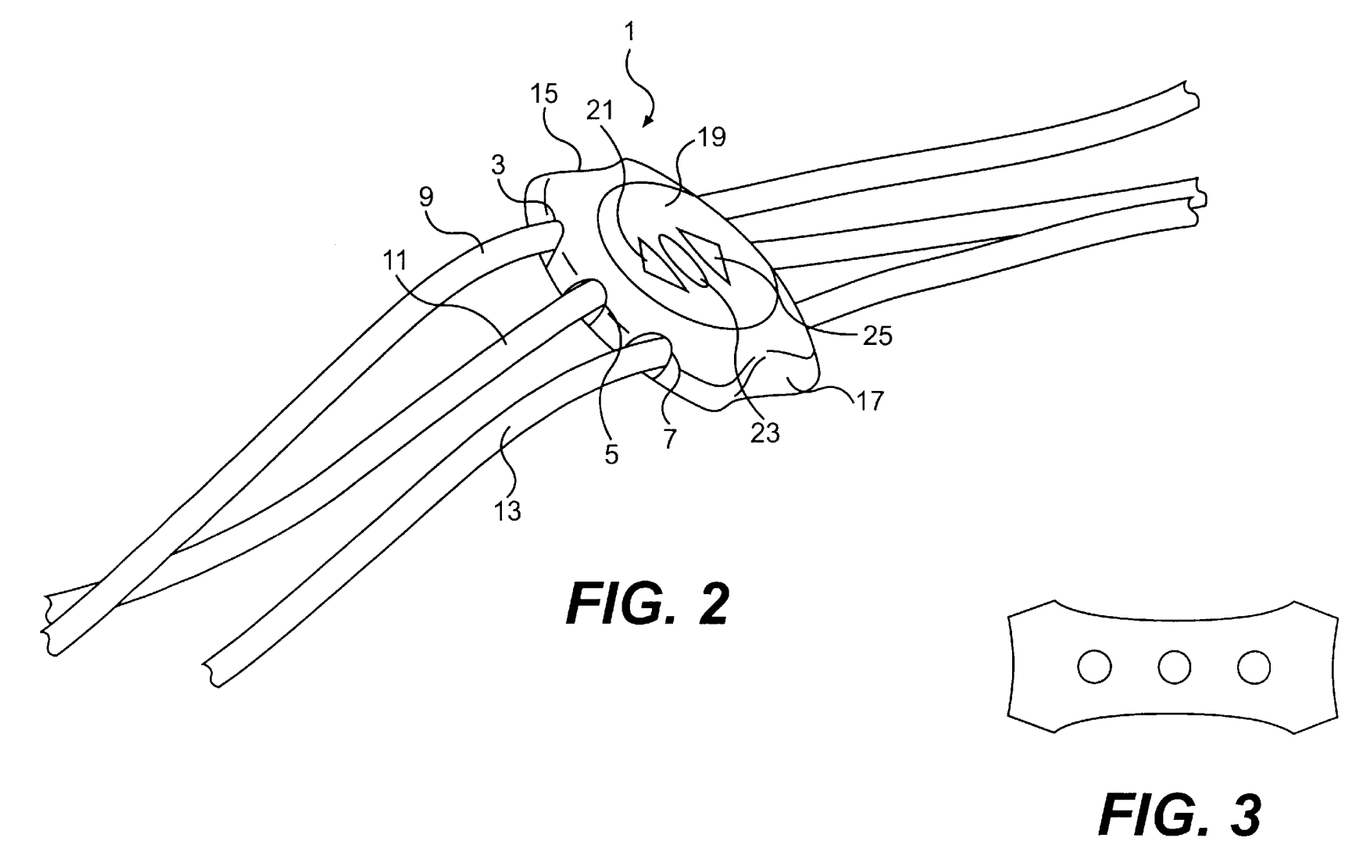
FIG. 2 represents a perspective view of the embodiment illustrated in FIG. 1.
FIG. 3 represents a cross-sectional view of the embodiment illustrated in FIG. 1.
Figure 4:
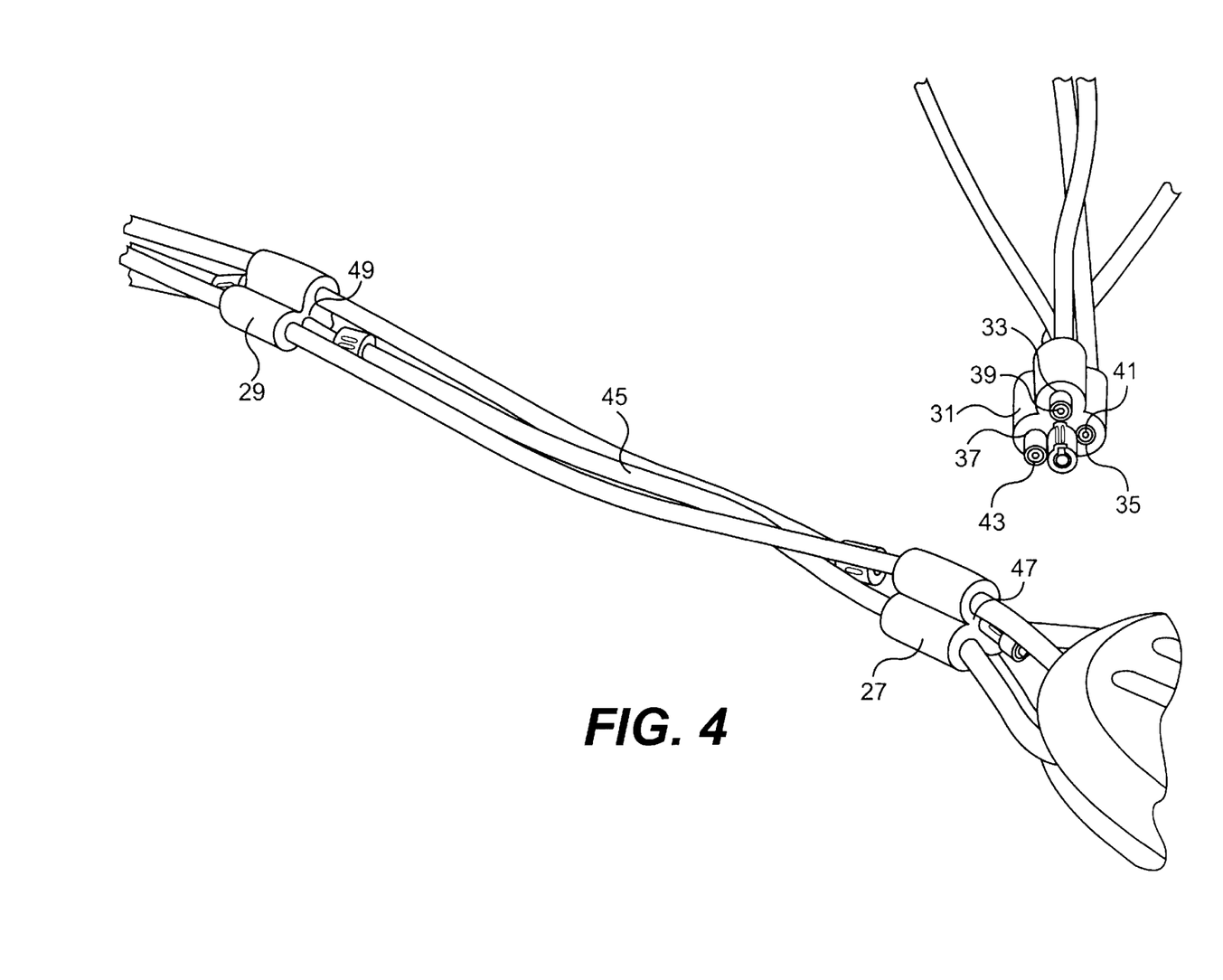
FIGS. 4–8 represent perspective views of another embodiment of a device for detangling a plurality of elongate flexible members according to the present invention in various configurations corresponding to various stages of an embodiment of a method according to the present invention.

FIGS. 1–3 illustrate an embodiment of a device according to the present invention that includes a single collar member. As described below in greater detail, a device according to the present invention may include a plurality of collar members. The collar member 1 shown in FIGS. 1–3 includes three elongate bores 3, 5, and 7. FIGS. 1 and 2 illustrate an elongate flexible member 9, 11, and 13 extending through each receiving passage. The elongate flexible members and the receiving passages have a round cross-sectional shape, as shown in cross-section in FIG. 3.

A collar according to the present invention may include grip-assisting members. For example, the embodiment shown in FIGS. 1 and 2 includes indented sidewalls 15 and 17 to provide a grip for a user. The collar member may also include grip-assisting elements on other surfaces. Along these lines, the collar member shown in FIGS. 1 and 2 includes a recess 19 at least on the top surface. The opposite, bottom surface may also include a similar recess.

A collar according to the present invention may additionally or alternatively include grip-assisting elements in addition to recesses. Along these lines, recess 19 shown in FIGS. 1 and 2 includes grip-assisting protrusions 21, 23, and 25. The side wall surfaces may also include grip-assisting protrusions. Such protrusions may be arranged on any surface of the collar member to enhance a user's grip as the user slides the collar member.

An embodiment such as that shown in FIGS. 1–3 or any embodiment of the present invention could only receive one elongate flexible member. Such an embodiment could still detangle or prevent the tangling of elongate flexible members.

FIGS. 4–8 illustrate another embodiment of a device according to the present invention. This embodiment includes a plurality of collar members such as collar members 27, 29, and 31 shown in FIG. 4. Each collar member includes three bores such as passages 33, 35, and 37 in collar member 31. The bores in the collar members shown in FIGS. 4–8 are arranged at the apexes of a triangle. Each receiving passage receives an elongate flexible member 39, 41, and 43.

Each collar member shown in FIGS. 4–8 has a generally triangular cross-sectional shape in a plane perpendicular to the longitudinal axis of the bores. The apexes of the triangular shape are rounded and the sides are indented, much as if the collar members were formed from three joined cylinders. This embodiment of the collar according to the present invention may, in fact, be so formed. Alternatively, this embodiment of the collar could be formed as a single member, such as through extrusion molding.

An embodiment of the present invention that includes more than one collar member on the elongate flexible members may include one or more elements to interconnect the collar members. FIGS. 4–8 illustrate an embodiment of interconnecting elements between collar members. The embodiment of the interconnecting elements shown in FIGS. 4–8 includes tethers, such as tether 45 connected between collar members 27 and 29.

The tether members may be formed of any suitable non-metallic material. For example, polymer materials could be utilized to form the tether members. For example, nylon or polyester could be used to form tether members. Natural materials could also be utilized, such as cotton. Also, composite materials could be utilized. These are just a few examples of materials that a tether could be made of. Other materials could also be utilized.

The tether could be braided, such as the tethers shown in FIGS. 4–8. Alternatively, a tether could be non-braided. For example, a mono-filament line, such as fishing line, could be utilized as a tether. A tether could also be formed of a tape-like or ribbon-like member.

The thickness of the tether may vary. Typically, the thickness is such that the tether may be easily moved. However, strength considerations may also come into play so that a tether will not tend to break. The thickness may also depend upon the material utilized to form the tether. Stronger materials may tend to be thinner, while weaker materials thicker. If a tether is ribbon or tape like, the tether may be thicker in one dimension and thinner in another.

Figure 5:
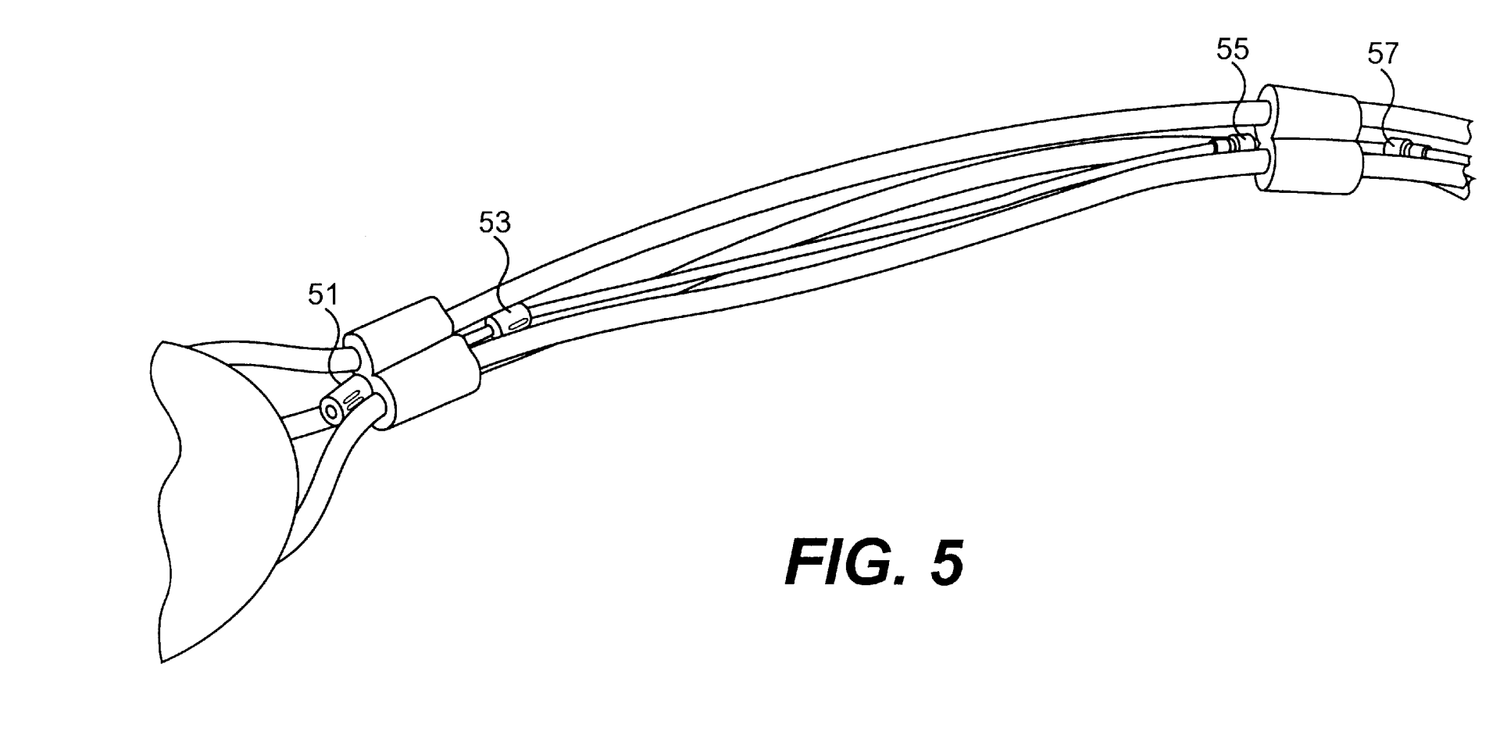

A tether may be anchored to a collar member in a variety of ways. In the embodiment shown in FIGS. 4–8, the collars include a tether receiving passage, such as tether receiving passages 47 and 49 in collar members 27 and 29 shown in FIG. 4. In such an embodiment, the "tethers" could actually include a single tether member that extends from collar to collar. Positioning elements could be arranged on the tether member to retain the collars in desired positions relative to the tether. For example, the tether shown in FIGS. 4–8 includes positioning members secured to the tether on opposite sides of each collar. Along these lines, FIG. 5 shows an embodiment of positioning members 51, 53, 55, and 57 on opposite sides of each collar member. The positioning members shown in FIGS. 4–8 have a larger outer dimension than the tether receiving passages in the collar members. The positioning members surround and grip the tether.

The tether members could be interconnected with the collar members in another manner. For example, one or more positioning members could be present within the tether receiving passage in the collar. Such positioning members could be inserted into the collar or the collar could be formed about the positioning members.

The tether could also interconnected with the collar from the outside of the collar. For example, an attachment element could be attached to the exterior of the collar and the tether associated with the attachment element. Along these lines, a screw eye could be extend from the collar, the tether could be fed through the screw eye and a positioning member such as those shown in FIGS. 4–8 could position the tether relative to the collar.

It is not necessary that the collars include a tether receiving passage. Such embodiments would typically include different tether positioning members than the embodiment shown in FIGS. 4–8. The collars could include an anchor that could attach the tether to the collar. For example, a tether positioning member could be integrated with the collar when the collar is formed. Alternatively, the tether positioning member could be attached to the collar, such as through a threaded portion screwed into the collar. In such embodiments, the tether typically could only have a length that it is desired the collars be separated by.

Figure 6:
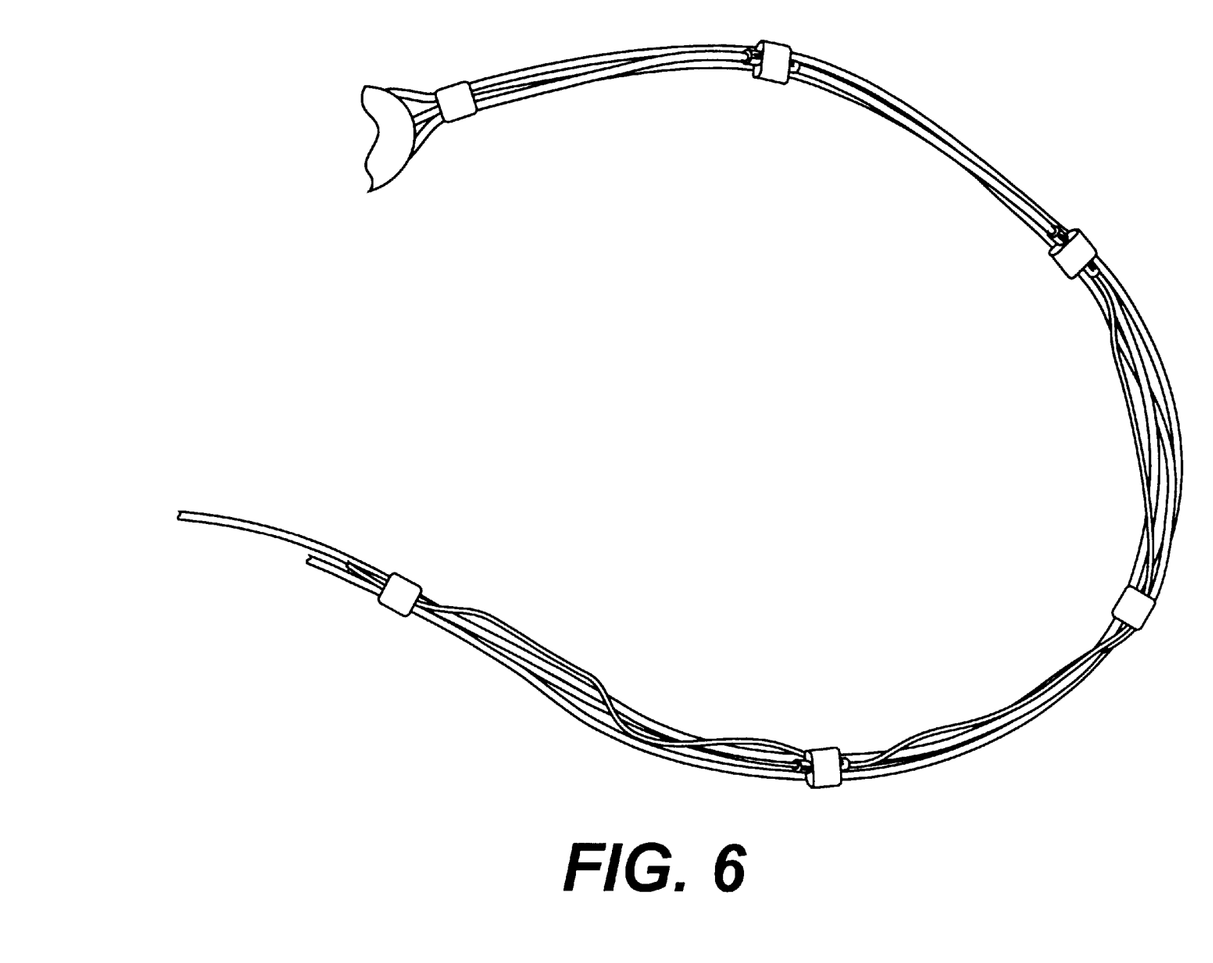

A tether member that connects two collar members may have any desirable length. Typically, a tether has a length no longer than the elongate flexible members to which the collar members are attached. A tether may have a length sufficient to maintain a desired spacing between the collar members. For example, the device according to the embodiment of the present invention shown in FIGS. 4–8 includes six collar members. Each collar member is connected to adjacent collar members by a tether member. Each tether has a length so as to permit the collar members to be equally spaced along the elongate flexible members upon sliding the collar members along the elongate flexible members so that the tether members are fully extended. FIG. 6 illustrates the tether members in a generally fully extended condition. It is not necessary for the tether members to be fully taught when extended. Having collar members interconnected by tether members can assist in detangling the elongate members since when the distal collar member slides along the elongate flexible members, the tether(s) will pull on other collar member(s) and slide the other collar members along the elongate flexible members.

Figure 7:
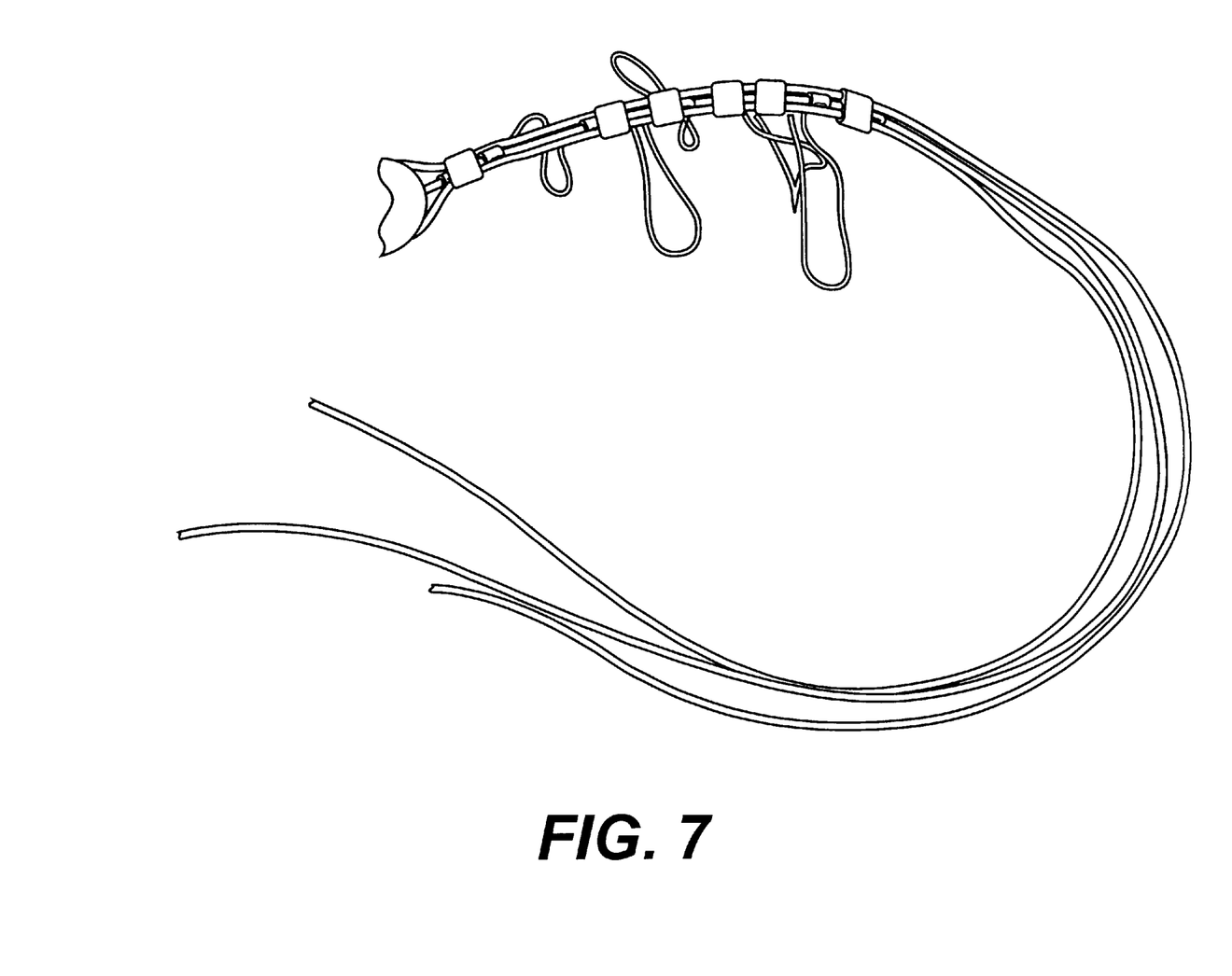
Figure 8:
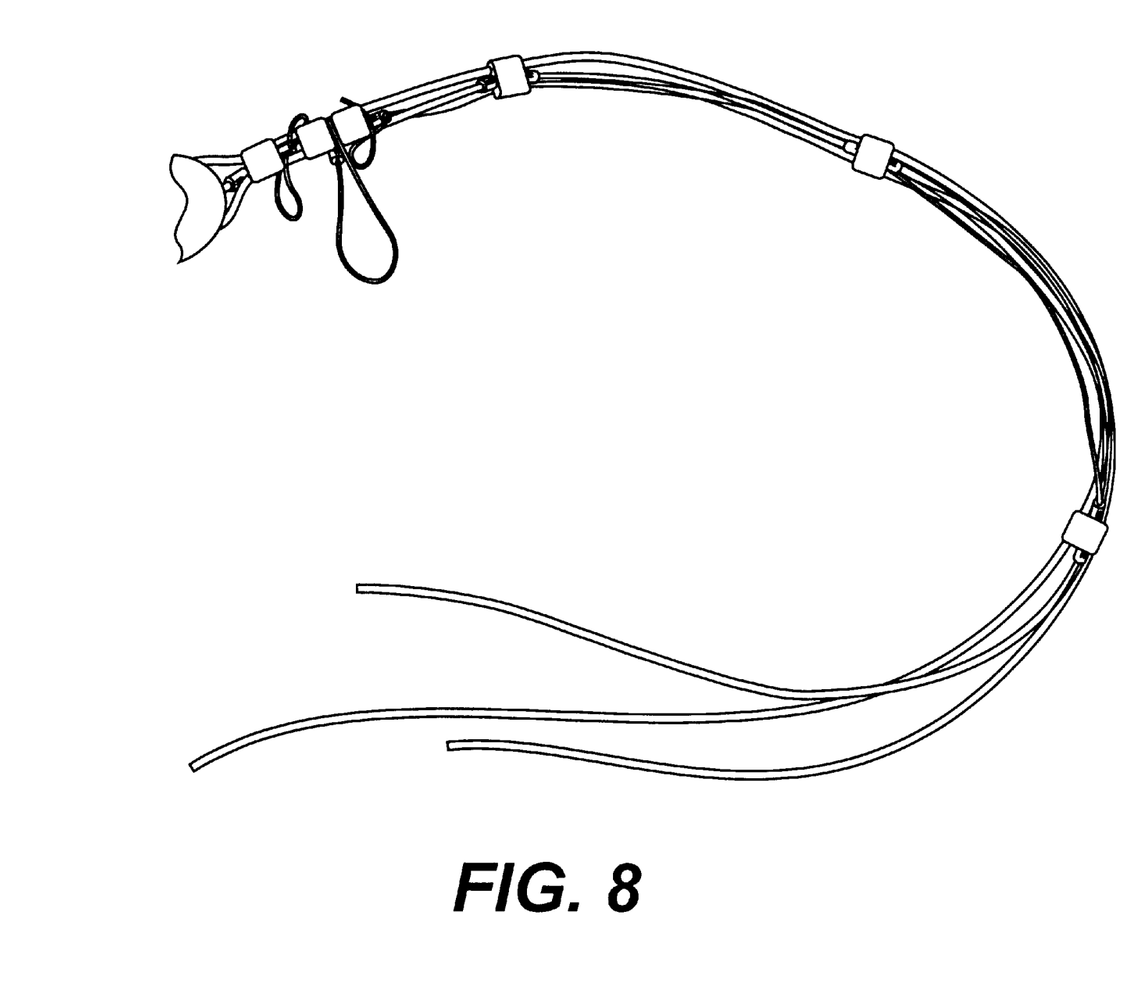

FIG. 6 illustrates this embodiment of the present invention with the collars in an extended position. Typically, the device would be stored in this position. On the other hand, FIG. 7 illustrates this embodiment of the invention in a retracted position, where all of the collar members have been moved to a location in the vicinity of one end of the elongate flexible members. As FIG. 7 illustrates, the tether members will be bunched up in the vicinity of the retracted collar members. The collar members may be moved toward one end of the elongate flexible members an amount sufficient to free up a desired amount of the elongate flexible members. FIG. 8 shows this embodiment of the present invention with the collars in a partially extended position. The intermediate position could be present during use of the elongate flexible members or as the collar members are moved between retracted and extended positions. With the tether members linking the collar members, as a distal collar member is moved away from the other congregated collar members, as depicted in FIG. 7, the tether members will pull the next collar member and the succeeding collar members until the tethers are as extended as much as desired. One of the collar members may be anchored in the vicinity of one end of the elongate flexible members to help maintain the collar members in an extended position.

Figure 9:
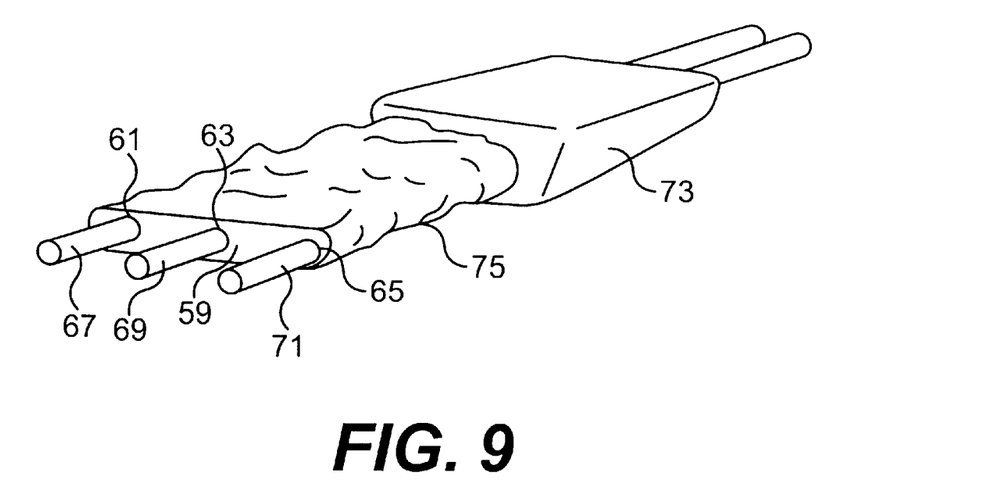
FIG. 9 represents a perspective view of another embodiment of a device for detangling a plurality of elongate flexible members according to the present invention.

Additionally or alternatively, the present invention may include a sheath or net member connected to the collar members. FIG. 9 illustrates such an embodiment of the present invention. The embodiment shown in FIG. 9 includes a slidable collar 59. The collar includes three elongate bores 61, 63, and 65 arranged in a line for receiving elongate flexible members 67, 69, and 71. The dimensions, materials and other aspects regarding collar member 59 could be as described above.

The embodiment shown in FIG. 9 also includes a second collar member 73. The collar member 73 may be attached anywhere along the elongate flexible members. According to one embodiment, the collar member is attached in the vicinity of an end of the elongate flexible members. The embodiment shown in FIG. 9 may include additional collar members.

The collar member 73 included in the embodiment shown in FIG. 9 could be similar to the collar member 59. Alternatively, the collar member 73 could be a variation of collar member 59. Furthermore, collar member 73 could include a housing from which the flexible members extend, typically referred to as a "yoke" in a cable assembly. Collar member 73 could be attached anywhere along the elongate flexible members. According to one embodiment, the collar member is attached in the vicinity of an end of the elongate flexible members.

A retractable sheath or net member 75 may be attached to the collar members. The sheath encloses the elongate flexible members when extended. Sliding at least one of the collar members away from the other typically extends the sheath. A sheath member could be similar to sheaths utilized with endotracheal tubes. The sheath could be attached to the collar members with adhesive, by welding, with clips or any other attachment means.

The sheath/net may be formed of any suitable non-metallic material. For example, the sheath/net could be formed of one or more polymers, nylon, polyester, or natural materials, such as cotton, or any combination of these materials. The sheath/net could extend between any number of collar members, similar to the tether described above. Also, the present invention could include one long sheath or net or a plurality of sheaths or nets.

To further help prevent tangling of the elongate flexible members, the present invention may include at least one elongate flexible member retainer. The present invention may include a retainer regardless of whether it includes one or more collar members. A retainer may engage and retain the elongate flexible members, thereby preventing them from becoming tangled. If the retainer is utilized in addition to one or more collar members, the collar member(s) may help to remove the elongate flexible members from the retainer as well as to reassociate the elongate flexible members with the retainer after their removal. According to such an embodiment, sliding a collar in one direction may result in removal of the elongate flexible members from the retainer and sliding the collar member in the opposite direction can result in reassociating the elongate flexible members with the retainer.

One embodiment of a retainer according to the present invention includes a plurality of grooves for retaining the elongate flexible members. The grooves have an opening narrower than the elongate flexible members. When the elongate flexible members are forced into the grooves, the narrower opening will retain the elongate flexible members. The elongate flexible members may be removed from the retainer by forcing them through the narrower openings. Typically, the openings are not so narrow that they prevent the elongate flexible members from being easily removed therefrom. Other embodiments of a retainer could include hooks or other elements to retain the elongate flexible members.

Figure 10:
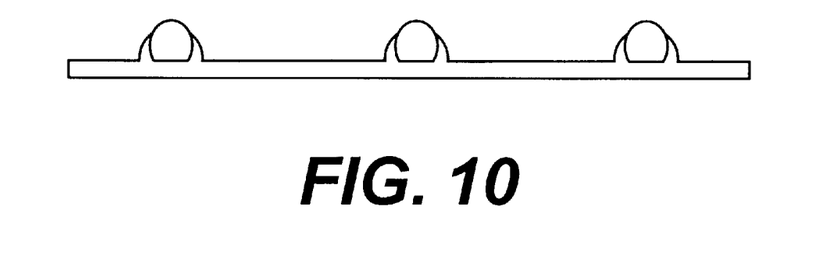
FIG. 10 represents a cross-sectional view of an embodiment of a flexible member retainer according to the present invention.
Figure 11:
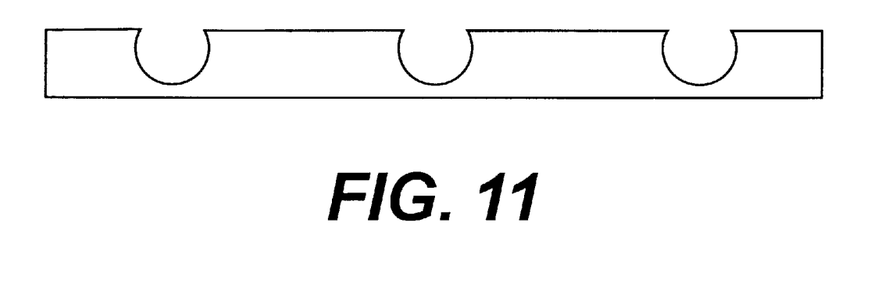
FIG. 11 represents a cross-sectional view of another embodiment of a flexible member retainer according to the present invention.

A retainer could be made of any material. Typically, a retainer is made of plastic or rubber. The retainer could be a single unitary member or a plurality of members joined together. FIGS. 10 and 11 illustrate cross-sections of two different exemplary embodiments of a retainer according to the present invention. Each embodiment shown includes a plurality of elongate bores having narrowed openings. The elongate flexible members may be removed from the retainer as needed. At times, during use of the elongate flexible members, only a portion of the length of the flexible members will need to be removed from the retainer. The retainers may be about as long as the elongate flexible members. Alternatively, the retainer may be shorter than the elongate flexible members. Such an embodiment could include a plurality of elongate flexible members.

Figure 12:
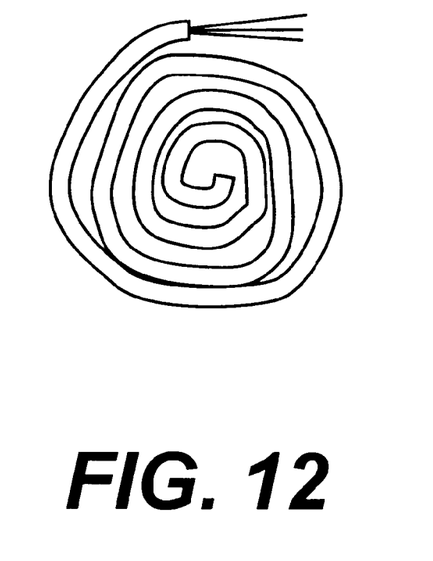
FIG. 12 represents an embodiment of flexible members retained by a flexible member retainer in a configuration of storage.
Figure 13:
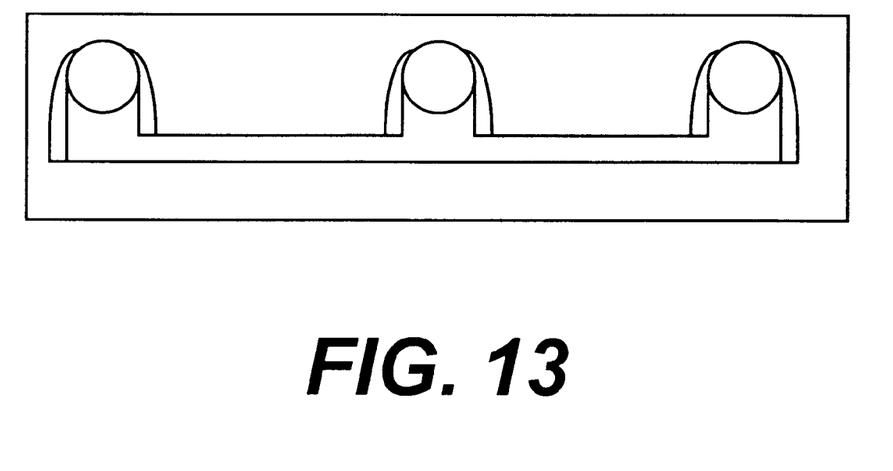
FIG. 13 represents a cross-sectional view of an embodiment of a flexible member retainer and collar combination according to the present invention.

For storage and to hold on to unneeded portions of the elongate flexible members, the retainer may be rolled up. FIG. 12 illustrates an embodiment of a retainer rolled up with elongate flexible members extending therefrom. As the elongate flexible members are needed, a sufficient amount of the retainer and elongate flexible members could be unrolled.

According to embodiments that include one or more collar members and one or more retainers, sliding a collar member along the elongate flexible members could remove the elongate flexible members from the retainer. According to some embodiments, a collar member could include a retainer receiving passage. FIG. 17 illustrates an embodiment of a collar member that includes passages for receiving the elongate flexible members and the retainer member. A separator is arranged between the elongate member receiving passages and the retainer receiving passage. A portion of the collar receives both the retainer and elongate flexible members in the same space.

As the collar is moved along the retainer in the direction where the elongate flexible members are retained by the retainer, the separator will cause the elongate flexible members to separate from the retainer. As the collar is moved in the opposite direction, the narrowing of the portion of the passage that receives both the elongate flexible members and the retainer will force the elongate flexible members back into the retainer. In this and any other embodiment, the retainer may act similar to a "zip-lock" closing plastic bag.

The present invention also includes a method for untangling elongate flexible members and/or preventing the tangling of elongate flexible members. The method includes sliding one or more collar members as described above along the elongate flexible members. As described above, some embodiments of a device according to the present invention include a plurality of collar members. Accordingly, some embodiments of a method according to the present invention can include sliding a plurality of collar members along the elongate flexible members. The one or more collar members may be moved toward one end of the elongate members to untangle the elongate flexible members or free them up for use. For storage, untangling, preventing tangling, or preparing the elongate flexible members for use, a plurality of collar members may be arranged in a spaced apart condition along the elongate flexible members. Sliding one collar member may result in applying force to one or more tethers and, thereby, apply force to move other collar members interconnected with the tether(s). Similarly, the method may include extending and retracting a sheath member.

Additionally, a method according to the present invention may include retaining the elongate flexible members with a retainer as described above to prevent the elongate flexible members from becoming tangled, whether or not the method includes sliding one or more collar members. If the method includes sliding a collar member, then sliding the collar member(s) can withdraw the elongate flexible members from the retainer and/or cause the elongate flexible members to be retained by the retainer. Furthermore, the method according to the present invention, whether or not it includes moving a collar member, can include rolling up and unrolling the retainer and the elongate flexible members.

As described above, the present invention is particularly useful with leads for operatively connecting electrodes and a defibrillator, monitor, and/or other electrotherapy device. A method according to the present invention can include connecting the elongate flexible members to and disconnecting the elongate flexible members from electrodes and/or a defibrillator or other electrotherapy device.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

I claim:

1. A device for detangling or preventing the tangling of a plurality of elongated flexible members, the device comprising:
   at least one slidable collar comprising at least one elongated bore for receiving at least one of the flexible members, wherein the slidable collar is slidable along the flexible members;
   a fixed collar comprising at least one elongated bore for receiving a plurality of flexible members, and wherein the fixed collar is fixed to the flexible members; and
   a plurality of retractable sheaths, each sheath surrounding at least a portion of two or more of the flexible members and fixed to the collar and the slidable collar, wherein each of the plurality are sheaths of adapted so as to surround a variable amount of the flexible members by sliding the slidable collar along the flexible member away from the fixed collar to extend at least one of the sheaths along the two or more flexible members so as to surround a variable amount of the flexible members.

2. The device according to claim 1, wherein the slidable collar comprises one bore for each flexible member.

3. The device according to claim 1, wherein the slidable collar comprises a plurality of parallel bores.

4. The device according to claim 1, wherein the collar slidable comprises three bores arranged in a triangle.

5. The device according to claim 1, comprising a plurality of the slidable collar and further comprising at least one tether for connecting adjacent collars.

6. The device according to claim 5, where the at least one tether are two tethers and are connected between adjacent collars.

7. The device according to claim 5, wherein one of the slidable collars is anchored to the flexible members in the vicinity of an end of the flexible members.

8. The device according to claim 1, further comprising:
   a flexible member retainer for retaining the flexible members, wherein sliding the slidable collar causes the flexible member retainer to release the flexible members when sliding in a first direction and causes the flexible member retainer to retain the flexible members when sliding in a second direction opposite to the first direction.

9. The device according to claim 8, wherein the flexible member retainer comprises a plurality of flexible member retaining grooves, each groove retaining one flexible member, each groove comprising an opening having a maximum width smaller than a maximum width of the flexible member the groove is to retain.

10. The device according to claim 8, wherein the at least one bore receives the flexible members and the flexible member retainer.

11. The device according to claim 10, wherein the slidable collar further comprises a separator for separating the flexible members and the flexible member retainer is arranged within the bore.

12. The device according to claim 8, further comprising:
a flexible member retainer receiving passage for receiving the flexible member retainer.

13. The device according to claim 8, wherein the flexible member retainer comprises an elongated member having a length substantially similar to the length of the flexible members.

14. The device according to claim 13, wherein a portion of the flexible member retainer that retains the flexible members is rolled up, and a portion of the flexible member retainer that is not retaining the flexible members is unrolled.

15. The device according to claim 1, wherein the flexible members are leads operatively connected to electrodes and a defibrillator.

16. A method for detangling a plurality of flexible members, the steps comprising:
sliding at least one slidable collar member along the flexible members, said at least one slidable collar member having a bore fore each of the flexible members, and
sliding the slidable collar member away from a fixed collar member fixed to the flexible members, thereby extending a plurality of retractable sheaths, each sheath surrounds at least a portion of two or more of the flexible members and is fixed to the slidable collar member and the fixed collar member so as to surround a variable amount of the flexible members.

17. The method according to claim 16, wherein a plurality of the slidable collar members are moved along the flexible members.

18. The method according to claim 17, further comprising:
arranging the plurality of slidable collar members spaced apart on the flexible members for storing the flexible members.

19. The method according to claim 18, further comprising:
sliding the plurality of slidable collar members toward an end of the flexible members to free up the flexible members for use.

20. The method according to claim 16, further comprising:
retaining the flexible members with a flexible member retainer as the slidable collar member is moved along the flexible members in a first direction; and
withdrawing the flexible members from the flexible member retainer as the slidable collar member is moved along the flexible members in a second direction.

21. The method according to claim 20, further comprising:
rolling-up the flexible member retainer and the retained flexible members after the flexible members are retained thereby.

22. The method according to claim 16, wherein the flexible members are lead wires for operatively connecting a defibrillator and electrodes, the method further comprising:
operatively connecting the flexible members to the defibrillator; and
operatively connecting the flexible members to the electrodes.

23. A method for preventing a plurality of flexible members from becoming tangled, the method comprising:
retaining the flexible members with a flexible member retainer comprising a plurality of flexible member retaining grooves, each groove retaining one flexible member, each groove comprising an opening having a maximum width smaller than a maximum width of the flexible member the groove is to retain; wherein
moving the flexible members in a first direction reassociates the flexible members and the retainer after removal, and moving the flexible members in a second direction opposite the first direction disassociates at least a portion of the flexible members from the retainer after insertion.

24. A device for preventing a plurality of flexible members from becoming tangled, the device comprising:
a flexible member retainer for retaining the flexible members, the flexible member retainer comprising a plurality of flexible member retaining grooves, each groove retaining one flexible member, each groove comprising an opening having a maximum width smaller than a maximum width of the flexible member the groove is to retain; wherein
said flexible member retainer for reassociating the flexible members after removal from the retainer when one of said flexible member retainer and the flexible members are moved in a first direction, and said flexible member retainer is for disassociating at least a portion of the flexible members from the retainer when one of said flexible member retainer and the flexible members are moved in a second direction opposite the first direction after insertion of the flexible members in said flexible member retainer.

25. The device according to claim 24, wherein at least one bore receives the flexible members and the flexible member retainer.

26. The device according to claim 24, wherein the flexible member retainer comprises an elongated member having length substantially similar to the length of the flexible members.

27. The device according to claim 24, wherein when in use the flexible members are released from the flexible member retainer, and wherein a portion of the flexible member retainer that retains the flexible members is rolled up, and a portion of the flexible member retainer that is not retaining the flexible members is unrolled.

* * * * *